United States Patent [19]

Bell

[11] 4,021,566
[45] May 3, 1977

[54] 2,5-DIMETHYL-1-PYRROLE-LOWER-ALKANECARBOXAMIDES

[75] Inventor: Malcolm Rice Bell, East Greenbush, N.Y.

[73] Assignee: Sterling Drug Inc., New York, N.Y.

[22] Filed: Oct. 21, 1975

[21] Appl. No.: 624,335

[52] U.S. Cl. .......................... 424/274; 260/326.43
[51] Int. Cl.² ........................................ A61K 31/40
[58] Field of Search ............... 260/326.43; 424/274

[56] References Cited

UNITED STATES PATENTS 3,903,110  9/1975  Freyermuth et al. ......... 260/326.43

*Primary Examiner*—Lewis Gotts
*Assistant Examiner*—Cary Owens
*Attorney, Agent, or Firm*—William G. Webb; B. Woodrow Wyatt

[57] ABSTRACT

2,5-Dimethyl-1-pyrrole-lower-alkanecarboxamides, prepared by reaction of a 3-$R_3$-4-$R_4$-2,5-hexanedione with either an ω-amino-lower-alkanonitrile or an ω-amino-lower-alkanecarboxamide, and if appropriate, hydrolysis of the resulting 2,5-dimethyl-3-$R_3$-4-$R_4$-1-pyrrole-lower-alkano-nitrile, have anti-secretory and anti-ulcer activities.

8 Claims, No Drawings

2,5-DIMETHYL-1-PYRROLE-LOWER-ALKANECARBOXAMIDES

BACKGROUND OF THE INVENTION a. Field of the Invention

This invention relates to 2,5-dimethyl-3-$R_3$-4-$R_4$-1-pyrrole-lower-alkanecarboxamides useful as anti-secretory and anti-ulcer agents.

b. Description of the Prior Art

Pyrrole-1-acetamide is described by Clemo and Ramage, J. Chem. Soc. 49–55 (1931) and by Sohl and Shriner, J. Am. Chem. Soc. 53, 4168–4170 (1931). However, no utility for the compound is suggested by either of these prior groups of workers.

SUMMARY OF THE INVENTION

This invention relates, in a composition of matter aspect, to 2,5-dimethyl-3-$R_3$-4-$R_4$-1-pyrrole-lower-alkane-carboxamides useful as anti-secretory and anti-ulcer agents.

The invention also relates, in a method aspect, to a method of reducing gastric secretion and incidence of ulcer formation in humans comprising administering an effective anti-secretory/anti-ulcer amount of a 2,5-dimethyl-3-$R_3$-4-$R_4$-1-pyrrole-lower-alkanecarboxamide.

In one aspect, the invention relates to a process for preparing a 2,5-dimethyl-3-$R_3$-4-$R_4$-1-pyrrole-lower-alkanecarboxamide comprising reacting a 3-$R_3$-4-$R_4$-2,5-hexanedione with an ω-amino-lower-alkanecarboxamide.

In another process aspect, the invention relates to a process for preparing a 2,5-dimethyl-3-$R_3$-4-$R_4$-1-pyrrole-lower-alkanecarboxamide comprising hydrolyzing a 2,5-dimethyl-3-$R_3$-4-$R_4$-1-pyrrole-lower-alkanonitrile.

DETAILED DESCRIPTION INCLUSIVE OF THE PREFERRED EMBODIMENTS

More specifically, this invention relates to 2,5-dimethyl-3-$R_3$-4-$R_4$-1-pyrrole-lower-alkanecarboxamides having the formula:

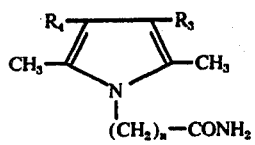

I where $R_3$ and $R_4$ are either both hydrogen or both methyl, and $n$ is one of the integers 1 and 2, except that when $n$ is 2, $R_3$ and $R_4$ are both methyl. The latter limitation on the scope of the invention is included in order to exclude an inactive species.

The compounds of formula I are prepared by reaction of an appropriate 3-$R_3$-4-$R_4$-2,5-hexanedione of formula II either with an ω-amino-lower-alkanecarboxamide of formula III or with an ω-amino-lower-alkanonitrile of formula IV followed by hydrolysis of the 2,5-dimethyl-3-$R_3$-4-$R_4$-1-pyrrole-lower-alkanonitrile of formula V resulting from reaction of the ω-amino-lower-alkanonitrile. The method is represented by the following reaction sequence:

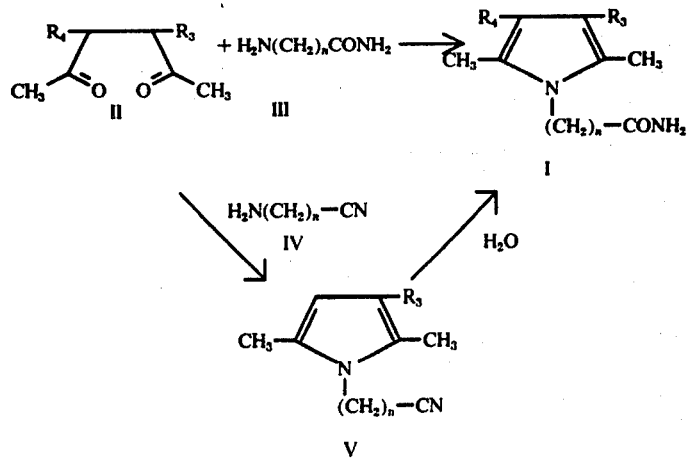

where $R_3$, $R_4$ and $n$ have the meanings given above.

Reaction of the 3-$R_3$-4-$R_4$-2,5-hexanedione of formula II with either the ω-amino-lower-alkanecarboxamide of formula III or the ω-amino-lower-alkanonitrile of formula IV is carried out by heating a solution of the reactants in acetic anhydride in the presence of a molar equivalent amount of sodium acetate.

Hydrolysis of the 3-$R_3$-4-$R_4$-2,5-dimethyl-1-pyrrole-lower-alkanonitriles of formula V is carried out by heating a solution of the nitrile in 90% aqueous sulfuric acid at a temperature in the range from 0° C. to 100° C.

The intermediates of formulas II, III and IV are all known compounds.

In standard biological test procedures, described generally by Shay et al., Gastroenterology 5, 43 (1945) and 26, 906 (1954) and by Selmici et al., Acta Physiol. Acad. Sci. Hung. 25 (1), 101–104 (1964); C.A. 62, 2130b (1965), the compounds of formula I have been found to possess anti-secretory and anti-ulcer activities and are thus useful as anti-secretory and anti-ulcer agents. Anti-secretory activity was determined in male albino Wistar rats weighing approximately 180 g. using the method described by Shay et al. which is described as follows: the rats were divided into medicated groups of at least five rats each and control groups of ten rats. The rats were medicated orally once daily for two days prior to stomach ligation and once again immediately following ligation. All drugs were administered as the free base, and control rats received only the vehicle of medication. The rats were housed individually in wire cages, food was withdrawn forty-eight hours prior to surgery, and water was withdrawn at the time of surgery. Laparotomy was performed under light ether anesthesia, the pyloric-duodenal junction was ligated, and the wound was closed with metal clips and sprayed with a protective surgical dressing. Five hours following surgery, the rats were sacrificed, the stomach was removed, and the gastric juice collected. The gastric fluid was centrifuged, and total volume, color, and volume of solids were recorded. The pH of the gastric fluid was then determined on a Beckamn pH meter, and the "free" and "total" hydrochloric acid content of each gastric sample was determined by titrating an aliquot of the gastric fluid (diluted to approximately 10 ml. with distilled water) by titrating with 0.1N sodium hydroxide against Toepfers reagent and phenolphthalein, respectively. By determining the milliequivalents of hydrochloric acid per milliliter of gastric juice and knowing the total volume of gastric juice secreted by each rat, the total acid output can be calculated. Since pH is a function of free acid, the activity of the test compounds can be evaluated by comparison of the mean free acid of medicated rats with the mean free acid of the controls, and the activity can thus be expressed in terms of percent inhibition of free acid.

The anti-ulcer activity of the compounds was determined using the reserpine-induced anti-ulcer test method, described by Selmici et al., which is described briefly as follows: male, albino, Sprague-Dawley rats, weighing approximately 300 g., were divided into medicated and control groups of at least five rats each, and one positive control group of five rats medicated with a known drug at the active dose was run with each experiment. The rats were medicated forty-eight, twenty-four, and one hour before receiving an injection of reserpine. All test drugs were administered orally in terms of base, and the control rats received only the vehicle of medication. The rats were housed individually in wire cages, and food was withdrawn twenty-four hours prior to injection of reserpine, while water was allowed ad libitum. One hour following the third medication, 5.0 mg. of reserpine per kilogram of body weight in a concentration of 5 mg./ml. was injected intramuscularly in each rat. Eighteen hours after injection the rats were sacrificed, their stomachs removed, opened along the greater curvature, rinsed in warm saline, and pinned to a cork board for gross observation. The stomachs were examined for the number and size of ulcerations located in the glandular portion of the stomach with the aid of a one millimeter grid ocular with a 10x dissecting microscope. The degree of ulceration was arbitrarily graded according to the number and size of the ulcers as follows:

0 <1 mm.$^2$ 1 point
1 <3 mm.$^2$ 2 points
≧ 3 mm.$^2$ 5 points.

The points were added together and divided by the number of rats in each group to give an ulcer score, and the difference in the mean scores of the medicated and control group was expressed as percent inhibition of ulceration. Alternatively, the results can be expressed as a ratio of the total number of rats with any degree of ulceration (as the numerator) to the total number of rats in the test group (as the denominator).

The compounds of formula I were thus found to inhibit secretion of gastric fluids and to inhibit reserpine-induced stomach ulceration when administered in rats in a dose range of from around 10 mg./kg. to around 200 mg./kg. These results indicate usefulness of the compounds in humans as anti-secretory/anti-ulcer agents when administered at a dose of 50 mg. per patient three or four times a day either alone or as the essential active ingredient. The compounds are preferably administered orally.

The actual determination of the numerical biological data definitive for a particular compound of formula I is readily determined by standard test procedures by technicians versed in pharmacological test procedures without the need for any extensive experimentation.

The compounds of formula I can be prepared for use by incorporation in unit dosage form as tablets or capsules for oral administration either alone or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

SPECIFIC EXEMPLARY DISCLOSURE

EXAMPLE 1

A mixture of 8.8 g. (0.062 mole) of 3,4-dimethyl-2,5-hexanedione [Criegee et al., Ber. 96 (10), 2704–2711 (1963)],6.83 g. (0.062 mole) of glycinamide hydrochloride and 5.06 g. (0.062 mole) of sodium acetate in 60 ml. of glacial acetic acid was refluxed under nitrogen for thirty minutes, then cooled, poured into excess ice water and filtered. The solid material was washed thoroughly with water, taken into ethyl acetate, the organic solution washed three times with water, then with brine, dried and the filtrate allowed to stand. The solid material which separated was collected and recrystallized twice from ethyl acetate to give 2.0 g. of 2,3,4,5-tetramethyl-1-pyrroleacetamide, m.p. 204°–205° C.

EXAMPLE 2

Following a procedure similar to that described in Example 1, a mixture of 22.8 g. (0.2 mole) of 2,5-hexanedione [Hori et al., Bull. Chem. Soc. Jap. 44 (10), 2856–2858 (1971)], 22 g. (0.2 mole) of glycinamide hydrochloride and 16.4 g. (0.2 mole) of sodium acetate in 250 ml. of acetic anhydride was refluxed for forty-five minutes and the product recrystallized from ethyl acetate to give 10.8 g. of 2,5-dimethyl-1-pyrroleacetamide, m.p. 172°–174° C.

EXAMPLE 3

Following a procedure similar to that described in Example 1, a mixture of 34 g. (0.24 mole) of 3,4-dimethyl-2,5-hexanedione, 30.6 g. (0.24 mole) of β-aminopropionitrile as the bis base fumarate and 196 g. (0.24 mole) of sodium acetate in 150 ml. of glacial acetic acid was refluxed under nitrogen for one hour and the product, 29 g. of β-(2,3,4,5-tetramethyl-1-pyrrole)propionitrile, used as such without further purification in the next step.

The crude nitrile isolated in the first step was added to a cold solution of 150 ml. of concentrated sulfuric acid and 15 ml. of water and the dark solution heated on a steam bath for ten hours. The mixture was then cooled, carefully neutralized with dilute sodium hydroxide, and the grayish solid which separated was collected by filtration, washed with water and dissolved in ethyl acetate. The organic solution, after washing with water and brine, drying and evaporation to dryness, afforded 15 g. of a red-brown solid which was chromatographed in a slurry of 50% ethyl acetate/benzene on 400 g. of Florisil (activated magnesium silicate). The column was eluted with a 30% solution of ethyl acetate in benzene, and the first 1.5 liters of eluate were discarded. Elution was then continued with 50% ethyl acetate/benzene, and the next three liters of eluate, on evaporation to dryness, afforded 8 g. of crude product which was recrystallized from ethyl acetate to give 4.95 g. of β-(2,3,4,5-tetramethyl-1-pyrrole)propionamide, m.p. 153°–154.5° C.

BIOLOGICAL TEST RESULTS

Results obtained for the compounds of Formula I in the anti-secretory and anti-ulcer activity tests described above are given in the table below. All doses were administered orally. For comparative purposes, data obtained in the anti-secretory activity test for the known reference compound, pyrrole-1-acetamide, described by Clemo et al. and by Sohl et al., ibid, which I have found also has anti-secretory activity, are also given.

| Example | Dose | Anti-Secretory | | Anti-Ulcer |
| | | pH | % Inhibition of Free Acid | % Inhibition |
| --- | --- | --- | --- | --- |
| Reference | 100 | 1.7 | 46 | — |
| 1 | 12.5 | 1.3 | 44 | — |
|  | 25 | 1.5 | 49 | 61 |
|  | 50 | 2.9 | 83 | 87 |
|  | 100 | 3.6 | 91 | 94 |
| 2 | 50 | 1.7 | 21 | 40 |
|  | 100 | 2.7 | 78 | — |
|  | 100 | 2.6 | 63 | — |
|  | 200 | 4.6 | 100 | — |
| 3 | 25 | — | — | 36 |
|  | 50 | — | — | 66 |
|  | 100 | 2.4 | 60 | — |

I claim:
1. A 2,5-dimethyl-3-$R_3$-4-$R_4$-1-pyrrole-loweralkanecarboxamide having the formula:

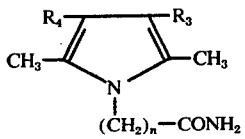

where $R_3$ and $R_4$ are either both hydrogen or both methyl, and $n$ is one of the integers 1 and 2, except that when $n$ is 2, $R_3$ and $R_4$ are both methyl.

2. A compound according to claim 1 where $n$ is 1.

3. 2,3,4,5-Tetramethyl-1-pyrroleacetamide according to claim 2.

4. 2,5-Dimethyl-1-pyrroleacetamide according to claim 2.

5. β-(2,3,4,5-Tetramethyl-1-pyrrole)propionamide according to claim 1.

6. A method of reducing gastric secretion and incidence of ulcer formation in humans comprising administering orally an effective anti-secretory/anti-ulcer amount of a 2,5-dimethyl-3-$R_3$-4-$R_4$-1-pyrrole-loweralkanecarboxamide according to claim 1 having the formula:

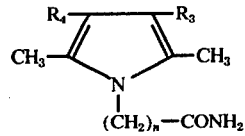

where $R_3$ and $R_4$ are either both hydrogen or both methyl, and $n$ is one of the integers 1 and 2, except that when $n$ is 2, $R_3$ and $R_4$ are both methyl.

7. The process for preparing a 2,5-dimethyl-3-$R_3$-4-$R_4$-1-pyrrole-lower-alkanecarboxamide according to claim 1 having the formula:

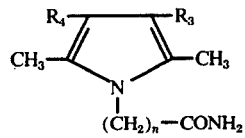

where $R_3$ and $R_4$ are either both hydrogen or both methyl, and $n$ is one of the integers 1 and 2, except that when $n$ is 2, $R_3$ and $R_4$ are both methyl which comprises reacting a 3-$R_3$-4-$R_4$-2,5-hexanedione having the formula:

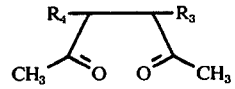

with an ω-amino-lower-alkanecarboxamide having the formula:

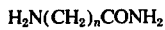

where $R_3$, $R_4$ and $n$ have the meanings given above.

8. The process for preparing a 2,5-dimethyl-3-$R_3$-4-$R_4$-1-pyrrole-lower-alkanecarboxamide according to claim 1 having the formula:

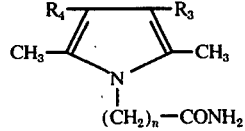

where $R_3$ and $R_4$ are either both hydrogen or both methyl, and $n$ is one of the integers 1 and 2, except that when $n$ is 2, $R_3$ and $R_4$ are both methyl which comprises hydrolyzing a 2,5-dimethyl-3-$R_3$-4-$R_4$-1-pyrrole-loweralkanonitrile having the formula:

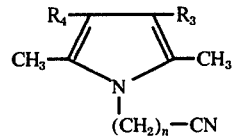

where $R_3$, $R_4$ and $n$ have the meanings given above.

* * * * *

UNITED STATES PATENT AND TRADEMARK OFFICE
CERTIFICATE OF CORRECTION

PATENT NO. : 4,021,566
DATED : May 3, 1977
INVENTOR(S) : Malcolm Rice Bell

It is certified that error appears in the above-identified patent and that said Letters Patent are hereby corrected as shown below:

Column 1, line 46, before "aspect" insert - -process- -.

Column 2, change formula V in the flow diagram to show:

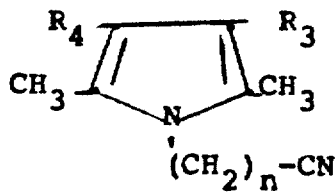

Signed and Sealed this

Twentieth Day of July 1982

[SEAL]

Attest:

GERALD J. MOSSINGHOFF

Attesting Officer

Commissioner of Patents and Trademarks